(12) United States Patent
Ming et al.

(10) Patent No.: US 8,604,073 B2
(45) Date of Patent: *Dec. 10, 2013

(54) ANTIMICROBIAL COMPOSITION

(75) Inventors: Xintian Ming, Bridgewater, NJ (US); Stephen J. Rothenburger, Neshanic Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 2107 days.

This patent is subject to a terminal disclaimer.

(21) Appl. No.: 11/389,824

(22) Filed: Mar. 27, 2006

(65) Prior Publication Data

US 2007/0225220 A1 Sep. 27, 2007

(51) Int. Cl.
- *A01N 43/50* (2006.01)
- *A61K 31/415* (2006.01)
- *A01N 37/52* (2006.01)
- *A61K 31/155* (2006.01)
- *A01N 33/12* (2006.01)
- *A61K 31/14* (2006.01)
- *C07D 233/54* (2006.01)
- *C07D 233/60* (2006.01)
- *C07C 277/00* (2006.01)
- *C07C 279/00* (2006.01)
- *C07C 211/00* (2006.01)
- *C07C 213/00* (2006.01)
- *C07C 215/00* (2006.01)
- *C07C 217/00* (2006.01)
- *C07C 221/00* (2006.01)
- *C07C 223/00* (2006.01)
- *C07C 225/00* (2006.01)

(52) U.S. Cl.
USPC ........ 514/400; 514/634; 514/642; 548/341.5; 564/230; 564/281

(58) Field of Classification Search
USPC ........ 514/400, 634, 642; 548/341.5; 564/230, 564/281
See application file for complete search history.

(56) References Cited

U.S. PATENT DOCUMENTS

| | | | |
|---|---|---|---|
| 3,069,320 A | 12/1962 | Vitalis | |
| 3,839,297 A | 10/1974 | Wasserman et al. | |
| 4,027,676 A | 6/1977 | Mattei | |
| 4,185,637 A | 1/1980 | Mattei | |
| 4,201,216 A | 5/1980 | Mattei | |
| 5,326,567 A | 7/1994 | Capelli | |
| 5,869,073 A | 2/1999 | Sawan et al. | |
| 6,468,521 B1 | 10/2002 | Pedersen et al. | |
| 7,196,117 B2 * | 3/2007 | Beltran et al. | 514/551 |
| 2005/0064210 A1 | 3/2005 | McGhee et al. | |
| 2005/0192547 A1 | 9/2005 | Modak et al. | |

FOREIGN PATENT DOCUMENTS

| | | |
|---|---|---|
| EP | 0272149 B1 | 6/1988 |
| JP | 59212405 | 5/1983 |
| JP | 98183705 | 12/1994 |
| WO | 94/19027 | 9/1994 |
| WO | WO 02/30204 A1 | 4/2002 |
| WO | 03/013454 | 2/2003 |
| WO | 03/043593 | 5/2003 |
| WO | 2006/084553 | 8/2006 |
| WO | 2006/125099 | 11/2006 |
| WO | 2006/125121 | 11/2006 |

OTHER PUBLICATIONS

Langerman, Chemical Health & Safety, 2004, Elsevier Inc., vol. 11, pp. 31-32.*
Kamal, Journal of the American Medical Association, 1991, American Medical Association, vol. 265, pp. 2364-2368.*
Block, S.S., Disinfection, Sterilization, and Preservation 4th ed. 1991, pp. 225, 232.
U.S. Appl. No. 11/132,543, filed May 19, 2005.
U.S. Appl. No. 11/132,946, filed May 19, 2005.
U.S. Appl. No. 11/133,007, filed May 19, 2005.
G.T. Pisko et al., "Combined Effect of Antibiotics and Surface-Active Substanges on Gramnegative Microorganisms", Abstract & Vrachebnoe Delo, No. 3, pp. 118-120.
E. Karaila, "The Combined Effect of Certain Surface-Active Agents and Antibiotics", From Kiljava Sanatorium and From the Department of Serology and Bacteriology, University of Helsinki; vol. 19, 1961; pp. 259-266.

* cited by examiner

*Primary Examiner* — Sarah Pihonak
(74) *Attorney, Agent, or Firm* — Roberts Mlotkowski Safran & Cole, P.C.

(57) ABSTRACT

An antimicrobial composition comprising (a) a cationic surfactant derived from the condensation of fatty acids and esterified dibasic amino acids, such as lauric arginate and (b) an antibiotic, such as of β-lactam antibiotics, polypeptides, quinolones. The composition may be used as a stand alone antimicrobial formulation, or in combination with medical articles or medical devices.

10 Claims, No Drawings

ANTIMICROBIAL COMPOSITION

FIELD OF INVENTION

This invention relates to a novel antimicrobial composition comprising (a) a cationic surfactant derived from the condensation of fatty acids and esterified dibasic amino acids and (b) an antibiotic; and to methods of preparation and uses thereof. More specifically, this invention relates to a novel antimicrobial composition comprising lauric arginate (LAE) and an antibiotic selected from the group consisting of β-lactam antibiotics, polypeptides and quinolones. The present invention also relates to medical devices utilizing such novel antimicrobial compositions.

BACKGROUND OF THE INVENTION

Each year, patients undergo a vast number of surgical procedures in the United States. Current data shows about twenty-seven million procedures are performed per year. Post-operative or surgical site infections ("SSIs") occur in approximately two to three percent of all cases. This amounts to more than 675,000 SSIs each year.

Whenever a medical device is used in a surgical setting, a risk of infection is created. The risk of infection dramatically increases for invasive or implantable medical devices, such as intravenous catheters, arterial grafts, intrathecal or intracerebral shunts and prosthetic devices, which create a portal of entry for pathogens while in intimate contact with body tissues and fluids. The occurrence of SSIs is often associated with bacteria that colonize on the medical device. For example, during a surgical procedure, bacteria from the surrounding environment may enter the surgical site and attach to the medical device. Bacteria can use the implanted medical device as a pathway to surrounding tissue. Such bacterial colonization on the medical device may lead to infection and morbidity and mortality to the patient.

A number of methods for reducing the risk of infection associated with invasive or implantable medical devices have been developed that incorporate antimicrobial agents into the medical devices. Such devices desirably provide effective levels of antimicrobial agent while the device is being used. For example, medical devices may contain antibiotics such as β-lactam antibiotics, polypeptides and quinolones. However, medical devices containing an antibiotic can suffer loss of efficacy resulting from the low stability of the antibiotic and more significantly, the increasing emergence of antibiotic-resistant bacteria. For instance, although β-Lactam antibiotics are known to be efficacious against S. aureus, the bacterial species that is believed to be the most common cause of surgical infections, these antibiotics are ineffective against antibiotic-resistant bacteria such as MRSA (methicillin-resistant Staphylococcus aureus) and MRSE (methicillin-resistant Staphylococcus epidermidis).

One potential solution to this problem is to use a combination of antibiotic and non-antibiotic antimicrobial agents to destroy or inhibit the growth of antibiotic-resistant bacteria. In particular, it is beneficial if the non-antibiotic antimicrobial agent has a differing pattern of bioavailability and mode of action from the antibiotic agent. The use of a blend of antimicrobial agents with different modes of action is often desirable to achieve a broader spectrum of antimicrobial activity against various organisms, especially against antibiotic-resistant bacteria.

US20050192547 A1 describes combinations of an antiseptic and an antibiotic in medical devices. In particular, this reference describes the use of (i) minocycline, triclosan, and a bismuth salt; (ii) minocycline, a chlorhexidine compound, and a bismuth salt; and (iii) minocycline, benzalkonium chloride, and a bismuth salt to deter the formation of antibiotic-resistant organisms.

There have been no reports to date on the use of a combination of (a) a cationic surfactant derived from the condensation of fatty acids and esterified dibasic amino acids and (b) an antibiotic. For example, LAE and an antibiotic are used in combination, resulting in an enhanced antimicrobial activity against a broader spectrum of the organisms, especially antibiotic-resistant bacteria.

SUMMARY OF THE INVENTION

Described herein is an antimicrobial composition comprising (a) a cationic surfactant derived from the condensation of fatty acids and esterified dibasic amino acids, such as lauric arginate, and (b) one or more antibiotic, such as β-Lactam antibiotics, polypeptides and quinolones. The composition may be used as a stand-alone antimicrobial formulation, or in combination with medical articles or medical devices.

DETAILED DESCRIPTION OF THE INVENTION

The present invention is directed to an antimicrobial composition comprising (a) a cationic surfactant derived from the condensation of fatty acids and esterified dibasic amino acids and (b) one or more antibiotic. More specifically, the present invention is directed to an antimicrobial composition comprising lauric arginate (LAE) and one or more antibiotic that may be used in combination with medical devices, wherein the antimicrobial properties of the device are improved by incorporation of lauric arginate (LAE) and antibiotics. It has been discovered that such composition exhibits a synergistic antimicrobial effect.

The use of the terms, "synergistic" is used in the present invention to mean a biological effect created from the application of two or more agents to produce a biological effect that is greater than the sum of the biological effects produced by the application of the individual agents.

The cationic surfactant described herein is derived from the condensation of fatty acids and esterified dibasic amino acids. More particularly, the cationic surfactant refers to a class of compounds derived from the condensation of fatty acids and esterified dibasic amino acids having the following formula:

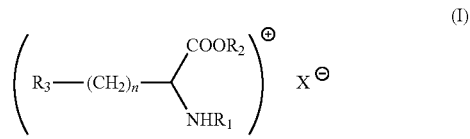

where X is Br, Cl, or $HSO_4$; $R_1$ is a linear alkyl chain from a saturated fatty acid or hydroxyacid having from 8 to 14 carbon atoms bonded to the alpha-amino acid group through an amidic bond; $R_2$ is a linear or branched alkyl chain from 1 to 18 carbon atoms or an aromatic group; $R_3$ is one of the following:

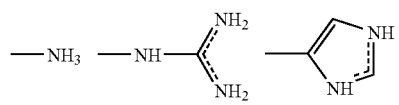

and n can be from 0 to 4.

A particular example of such class of cationic surfactant is lauric arginate (LAE—manufactured by Lamirsa Laboratories, Barcelona, Spain). Lauric arginate, a cationic preservative derived from lauric acid and arginine, in particular, the ethyl ester of the lauramide of the arginine monohydrochloride, can be used to protect against the growth of microorganisms. The chemical structure of LAE is described in formula (III):

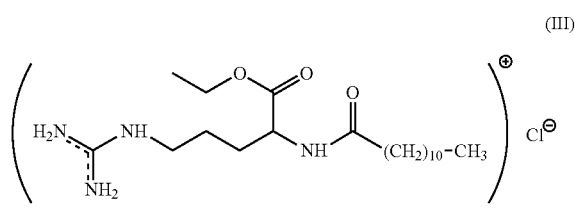

Antibiotic referred to herein is a substance derived naturally from fungi or bacteria, or synthetically, that destroys or inhibits the growth of microorganisms. General classes of antibiotic include, but are not limited to, β-lactam antibiotics, polypeptides and quinolones. More specifically, the antibiotic may be selected from the group consisting of penicillins, cephalosporins, carbepenems, beta-lactams antibiotics, aminoglycosides, amphenicols, ansamycins, macrolides, lincosamides, glycopeptides, polypeptides, tetracylines, chloramphenicol, quinolones, fucidins, sulfonamides, sulfones, nitrofurans, diaminopyrimidines, trimethoprims, rifamycins, oxalines, streptogramins, lipopeptides, ketolides, polyenes, azoles, echinocandins, and any combination thereof. Antibiotics, in particular, β-lactam antibiotics, polypeptides, quinolones, or mixtures thereof, are especially potent against a broad spectrum of microorganisms, i.e., effective against a variety of microorganisms, particularly, against both gram-negative and gram-positive bacteria.

In one particular set of non-limiting embodiments, the antimicrobial composition comprises (a) a cationic surfactant derived from the condensation of fatty acids and esterified dibasic amino acids and (b) one or more antibiotic, as a stand-alone antimicrobial composition formulation, independent of any medical devices or specific applications. Formulation of the antimicrobial composition according to the present invention may be of liquid (e.g. solutions) or solid form (e.g. powders). For instance, the antimicrobial composition may be applied directly to a wound.

It has been found that the combination of LAE with one or more antibiotic has better activity than LAE alone or the antibiotic alone, and that LAE functions as an antimicrobial enhancing agent. The antimicrobial composition according to the present invention is characterized by its synergistic effect, which refers to a phenomenon whereby the effect of two or more components together is greater then the sum of their effects when used individually. It has now been found that the antimicrobial activity of the combination of LAE with one or more antibiotic is higher than the activity displayed by each of the components when used individually at the same dosage. This enhancement of activity by LAE may be explained by its mode of action that damages the cytoplasmic membrane of the microorganisms.

This enhanced antimicrobial activity allows the composition to have potent efficacy against a wide range of microorganisms at levels where the two compounds used individually would not be as effective. The use of this combination it believed to be effective against a broader antimicrobial spectrum including, but not limited, *Tinea pedis, Tinea unguium,* *Tinea cruris,* or *Tinea capitis, S. aureus,* MRSA, MRSE, GISA, *S. epidermidis, E. coli, P. aeruginosa, K. pneumoniae, B. cepacia, E. cloacae, S. marcescens, S. pyogenes, S. agalacticae, E. faecalis*-Vancomycin Resistant, *E faecium, C. albicans* and *B. subtilis, Salmonella* sp., *Proteus* sp., *Acinetobacter* sp. *Aspergillus niger.*

To exhibit the synergistic effect of the antimicrobial composition, a stand alone antimicrobial composition may comprise LAE in an amount from about 0.001% to about 1% by weight based on the total weight of the composition, and the antibiotic in an amount from about 0.001% to about 1% by weight relative to total weight of the composition. More preferably, the antimicrobial composition of the invention comprises LAE in an amount from about 0.01% to about 0.1% by weight based on the total weight of the composition, and the antibiotic in an amount from about 0.01% to about 0.1% by weight relative to total weight of the composition.

In another set of non-limiting embodiments, the present invention provides medical devices incorporated with the antimicrobial composition. The terms "incorporate", "incorporated", or "incorporating", as used herein, refer to combining the composition with the medical device by physical or chemical means. Examples include, but are not limited to, impregnating, dipping, soaking or coating a medical device with the antimicrobial composition or preparing the medical device by adding the antimicrobial composition to the material that the medical device is made from. The medical devices that may be treated according to the invention are either fabricated from or coated or treated with a biomedical polymer and include, but are not limited to, microcapsules, dressings, implants, wound closures, staples, meshes, controlled drug delivery systems, wound coverings, fillers, sutures, tissue adhesives, tissue sealants, absorbable and non-absorbable hemostats, catheters including urinary catheters and vascular catheters (e.g., peripheral and central vascular catheters), wound drainage tubes, arterial grafts, soft tissue patches (such as polytetrafluoroethylene ("PTFE") soft tissue patches), gloves, shunts, stents, tracheal catheters, wound dressings, guide wires and prosthetic devices (e.g., heart valves and LVADs). The present invention may be further applied to medical articles that have been prepared according to U.S. Pat. Nos. 3,839,297; 4,027,676; 4,185,637 and 4,201,216, the contents of which is hereby incorporated by reference herein as if set forth in its entirety.

For example, where the medical article is a hydrogel such as Nu-Gel® hydrogel (commercially available from Johnson & Johnson Medical, a divison of Ethicon, Inc., Gargrave, U.K.), the amount of LAE may be from about 0.001-100 µg/cm², and preferably from about 0.01-50 µg/cm², while the amount of antibiotic may be from about 0.001 to 1000 µg/cm², and preferably from about 0.01 to 100 µg/cm².

While the following examples demonstrate certain embodiments of the invention, they are not to be interpreted as limiting the scope of the invention, but rather as contributing to a complete description of the invention.

EXAMPLE 1

Evaluation of the Synergistic Effect of Antibiotic-LAE Composition in Vitro

The synergistic effect of LAE and an antibiotic is illustrated by the results shown in Table 1 and Table 2 and was determined by the following protocol. Lauric arginate (LAE) and antibiotic solutions were prepared at a concentration of 1000 ppm in sterile saline. Sequential sterile saline dilutions of the above two stock solutions were then prepared. A portion of 0.05 ml of each dilution was added to 0.95 ml of bacterial culture (trypticase soy broth containing $10^6$ CFU/ml). Controls contained similar amounts of saline in the test culture with neither antibiotics nor LAE. The test cultures were incubated at 37° C. for 24 hr, and the total viable bacteria were numerated by plate count on Trypticase® soy agar (BBL) containing inactivating agent. The plates were incubated at 37° C. for 48 hr and reported as colony forming unit/ml (CFU/ml). Using *S. aureus* as an example, the control cultures were grown to $1.1 \times 10^9$ cfu/ml in the absence of lauric arginate (LAE) or antibiotics.

TABLE 1

Synergistic effect of LAE with antibiotics against *S. aureus* in vitro

| Treatment | *S. aureus* CFU/ml |
|---|---|
| Control | $1.2 \times 10^9$ |
| LAE 10 ppm | $1.0 \times 10^9$ |
| Cefazolin (CF) 10 ppm | $2.5 \times 10^8$ |
| LAE/CF 10/10 ppm | <10 |
| Polymixin B (PY)10 ppm | $3.2 \times 10^8$ |
| LAE/PY 10/10 ppm | <10 |
| Levofloxacin (LV) 0.2 ppm | $4.7 \times 10^3$ |
| LAE/LV 10/0.2 ppm | <10 |

TABLE 2

Synergistic effect of LAE with antibiotics against *P. aeruginosa* in vitro

| Treatment | *P. aeruginosa* CFU/ml |
|---|---|
| Control | $1.3 \times 10^9$ |
| LAE 10 ppm | $1.0 \times 10^9$ |
| Polymixin B (PY) 1 ppm | $8.5 \times 10^8$ |
| LAE/PY 10/1 ppm | <10 |
| Levofloxacin (LV) 1 ppm | $7.1 \times 10^6$ |
| LAE/LV 10/1 ppm | <10 |

These results show the synergistic effect of lauric arginate (LAE) and the antibiotic. The addition of lauric arginate (LAE) alone at 10 ppm resulted in less than half log reduction compared to the controls. The addition of antibiotics alone resulted in less than 1 log reduction of viable bacteria for 10 ppm Cefazolin and 10 ppm Polymixin B, and a 5 log reduction for 0.2 ppm Levofloxacin compared to the control. As shown in Table 1 and 2, the combination of LAE and the antibiotic provided much greater log reduction (9 log) against both Gram positive and Gram negative bacteria compared to use of LAE or the antibiotic alone at similar concentration (0.2-5 log).

EXAMPLE 2

The synergistic effects of LAE and an antibiotic against clinically significant resistant bacteria methicillin-resistant *Staphylococcus aureus* (MRSA) and methicillin-resistant *Staphylococcus epidermidis* (MRSE) in vitro were determined using the same protocol as described in Example 1. The results are presented in Table 3. MRSE used are MRSE 700563 and MRSE 51625. MRSA used are MRSA-002 and MRSA-006. (from internal culture collection)

TABLE 3

Synergistic effect of LAE with antibiotics against methicillin-resistant *S. aureus* (MRSA) and methicillin-resistant *S. epidermidis* (MRSE) in vitro.

| | CFU/ml | |
|---|---|---|
| Treatment | MRSA-002 | MRSA-006 |
| Control | $1.4 \times 10^9$ | $1.6 \times 10^9$ |
| LAE 5 ppm | $5.0 \times 10^6$ | $6.2 \times 10^8$ |
| Cefazolin (CF) 100 ppm | $1.1 \times 10^9$ | $1.4 \times 10^5$ |
| LAE/CF 5/100 ppm | <10 | <10 |
| Polymixin B (PY)100 ppm | $1.2 \times 10^9$ | $1.2 \times 10^9$ |
| LAE/PY 5/50 ppm | <10 | <10 |
| Treatment | MRSE 700563 | MRSE 51625 |
| Control | $1.8 \times 10^9$ | $2.0 \times 10^9$ |
| LAE 5 ppm | $4.0 \times 10^8$ | $1.2 \times 10^9$ |
| Cefazolin (CF) 100 ppm | $1.5 \times 10^8$ | $1.5 \times 10^6$ |
| LAE/CF 5/100 ppm | <10 | <10 |
| Polymixin B (PY)100 ppm | $1.2 \times 10^9$ | $6.2 \times 10^8$ |
| LAE/PY 5/100 ppm | <10 | <10 |

EXAMPLE 3

The synergistic effect of a composition of LAE and an antibiotic was observed when the composition was incorporated into a medical device such as Nu-Gel® hydrogel (Johnson & Johnson medical, Divison of Ethicon, Inc. Gargrave, U.K.). Solutions containing LAE and/or an antibiotic were prepared as in Example 1. The Nu-Gel® hydrogel was cut into 0.7×0.7 cm squares and were immersed into the stock solutions of LAE and antibiotics prepared as described in Examples 1 and 2 for 10 min. The treated Nu-Gel® hydrogel squares were dried at room temperature for 10 min and then placed onto TSA agar plates inoculated with methicillin-resistant *Staphylococcus aureus* (MRSA) and methicillin-resistant *Staphylococcus epidermidis* (MRSE). The plates were incubated at 37° C. for 48 hours.

The zone of inhibition, which is defined as the average distance in millimeter from four edges of the square and four edges of the clear zone around the square, was measured. The results shown in Tables 4, indicate that the combination of lauric arginate (LAE) and an antibiotic resulted in improved antimicrobial activity against methicillin-resistant *S. aureus* (MRSA) and methicillin-resistant *S. epidermidis* (MRSE), compared to the use of LAE and the antibiotic individually. The untreated Nu-Gel® hydrogel square and the Nu-Gel® hydrogel square treated with LAE or an antibiotic alone exhibited no zone of inhibition, while the squares treated with the combination of LAE and an antibiotic showed a distinct zone of inhibition.

This synergistic effect demonstrates that a medical device with good efficacy against antibiotic-resistant bacteria may be made by incorporating a combination of LAE and one or more antibiotic at concentrations of the agents that would be effective if used alone.

TABLE 4

Synergistic effect of LAE and antibiotics displayed in Nu-Gel ® hydrogel

| | Zone of inhibition (mm) | |
|---|---|---|
| Treatment | MRSA 006 | MRSE 700563 |
| Control | 0 | 0 |
| LAE 6 ug/cm$^2$ | 0 | 0 |

TABLE 4-continued

Synergistic effect of LAE and antibiotics
displayed in Nu-Gel ® hydrogel

| Treatment | Zone of inhibition (mm) | |
|---|---|---|
| | MRSA 006 | MRSE 700563 |
| Cefazolin (CF) 60 ug/cm$^2$ | 0 | 0 |
| Polymixin B (PY) 60 ug/cm$^2$ | 0 | 0 |
| LAE 6 ug/cm$^2$ + CF 60 ug/cm$^2$ | 4.1 | 9.6 |
| LAE 6 ug/cm$^2$ + PY 60 ug/cm$^2$ | 2.0 | 2.6 |

What is claimed is:

1. A medical device having an antimicrobial composition comprising:
   a medical device;
   a cationic surfactant derived from the condensation of fatty acids and esterified dibasic amino acids, according to the following formula:

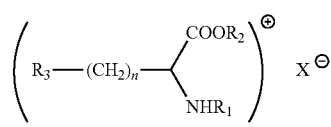

(I)

where X is Br, Cl, or HSO$_4$; R$_1$ is a linear alkyl chain from a saturated fatty acid or hydroxyacid having from 8 to 14 carbon atoms bonded to the alpha-amino acid group through an amidic bond; R$_2$ is a linear or branched alkyl chain from 1 to 18 carbon atoms or an aromatic group; R$_3$ is one of the following:

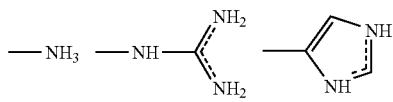

and n ranges from 0 to 4; and
   at least one antibiotic selected from the group consisting of penicillins, cephalosporins, carbepenems, other beta-lactam antibiotics, aminoglycosides, amphenicols, ansamycins, macrolides, lincosamides, glycopeptides, polypeptides, tetracylines, chloramphenicol, quinolones, fucidins, sulfonamides, sulfones, nitrofurans, diaminopyrimidines, trimethoprims, rifamycins, oxalines, streptogramins, lipopeptides, ketolides, polyenes, azoles, echinocandins, and any combination thereof.

2. The medical device of claim 1, wherein the cationic surfactant is lauric arginate, according to the following formula:

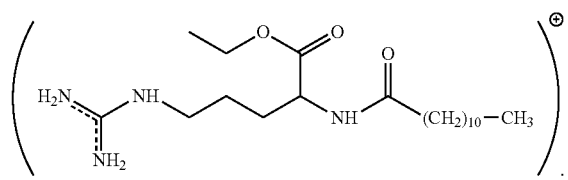

3. The medical device of claim 1, wherein the antibiotic is selected from the group consisting of β-lactam antibiotics, polypeptides, quinolones, and any combination thereof.

4. The medical device of claim 1, wherein the antibiotic is cefazolin, polymixin B, levofloxacin and any combination thereof.

5. A medical device having an antimicrobial composition comprising:
   a medical device;
   lauric arginate according to the following formula:

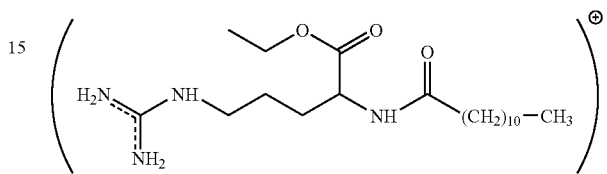

and
   at least one antibiotic selected from the group consisting of penicillins, cephalosporins, carbepenems, other beta-lactam antibiotics, aminoglycosides, amphenicols, ansamycins, macrolides, lincosamides, glycopeptides, polypeptides, tetracylines, chloramphenicol, quinolones, fucidins, sulfonamides, sulfones, nitrofurans, diaminopyrimidines, trimethoprims, rifamycins, oxalines, streptogramins, lipopeptides, ketolides, polyenes, azoles, echinocandins, and any combination thereof.

6. The medical device of claim 5, wherein the antibiotic is selected from the group consisting of β-lactam antibiotics, polypeptides, quinolones, and any combination thereof.

7. The medical device of claim 5, wherein the antibiotic is cefazolin, polymixin B, levofloxacin and any combination thereof.

8. A medical device incorporating an antimicrobial composition comprising:
   a medical device;
   between about 5-10 ppm of lauric arginate; and
   between about 0.2-100 ppm of an antibiotic selected from the group consisting of cefazolin, polymixin B and levofloxacin, relative to the total weight of the composition.

9. A medical device incorporating an antimicrobial composition which is made by a process comprising impregnating, dipping, coating or soaking said medical device with an antimicrobial composition comprising between about 5-10 ppm of lauric arginate and between about 0.2-100 ppm of an antibiotic selected from the group consisting of cefazolin, polymixin B and levofloxacin, relative to the total weight of the composition.

10. The medical device of claim 9, wherein the medical device is selected from the group consisting of microcapsules, wound dressings, implants, wound closures, staples, meshes, controlled drug delivery systems, wound coverings, fillers, sutures, tissue adhesives, tissue sealants, absorbable and non-absorbable hemostats, catheters, wound drainage tubes, arterial grafts, soft tissue patches, gloves, shunts, stents, guide wires and prosthetic devices.

* * * * *